(12) United States Patent
Rank

(10) Patent No.: US 9,244,042 B2
(45) Date of Patent: Jan. 26, 2016

(54) VIBRATION CONDITION MONITORING SYSTEM AND METHODS

(71) Applicant: General Electric Company, Schenectady, NY (US)

(72) Inventor: Brandon James Rank, Minden, NV (US)

(73) Assignee: General Electric Company, Schenectady, NY (US)

( * ) Notice: Subject to any disclaimer, the term of this patent is extended or adjusted under 35 U.S.C. 154(b) by 245 days.

(21) Appl. No.: 13/956,276

(22) Filed: Jul. 31, 2013

(65) Prior Publication Data

US 2015/0039250 A1 Feb. 5, 2015

(51) Int. Cl.
H04R 29/00 (2006.01)
G01N 29/14 (2006.01)
G01N 29/44 (2006.01)
G01N 29/46 (2006.01)

(52) U.S. Cl.
CPC ............ *G01N 29/14* (2013.01); *G01N 29/4454* (2013.01); *G01N 29/46* (2013.01); *H04R 29/00* (2013.01); *G01N 2291/2693* (2013.01); *G01N 2291/2696* (2013.01)

(58) Field of Classification Search
None
See application file for complete search history.

(56) References Cited

U.S. PATENT DOCUMENTS

| | | | |
|---|---|---|---|
| 5,602,757 A | 2/1997 | Haseley et al. | |
| 6,053,047 A | 4/2000 | Dister et al. | |
| 6,484,109 B1 | 11/2002 | Lofall | |
| 7,283,914 B2 | 10/2007 | Poorman et al. | |
| 7,317,994 B2 | 1/2008 | Iyer et al. | |
| 2005/0044561 A1* | 2/2005 | McDonald | 725/18 |
| 2005/0197724 A1* | 9/2005 | Neogi | 381/56 |
| 2005/0257618 A1 | 11/2005 | Boken | |
| 2007/0038393 A1 | 2/2007 | Borah et al. | |
| 2007/0055500 A1* | 3/2007 | Bilobrov | 704/217 |
| 2009/0012638 A1* | 1/2009 | Lou | 700/94 |

(Continued)

FOREIGN PATENT DOCUMENTS

WO 9613011 5/1996
WO 9960351 11/1999

(Continued)

OTHER PUBLICATIONS

International Search Report and Written Opinion issued in connection with corresponding PCT Application No. PCT/US2014/043064 on Nov. 4, 2014.
Cano et al., "A Review of Algorithms for Audio Fingerprinting," pp. 1-12 (No Date).

(Continued)

*Primary Examiner* — Thang Tran
(74) *Attorney, Agent, or Firm* — Fletcher Yoder, P.C.

(57) ABSTRACT

In one embodiment, a diagnostics system is provided. The diagnostics system include a detection system configured to capture acoustic information and contextual information related to a machine component defect. A computing system is coupled to a processor configured to receive the acoustic information and the contextual information from the detection system, select one or more algorithms based at least in part on the contextual information, and retrieve and execute the one or more algorithms to extract one or more characteristic features of the acoustic information. The processor is further configured to generate an acoustic fingerprint based at least in part on the one or more characteristic features of the acoustic information, such that the one or more characteristic features correspond to the machine component defect.

20 Claims, 3 Drawing Sheets

(56) References Cited

U.S. PATENT DOCUMENTS

| | | | |
|---|---|---|---|
| 2010/0049343 A1* | 2/2010 | Jaiswal et al. | 700/94 |
| 2010/0060436 A1* | 3/2010 | Kangas et al. | 340/384.5 |
| 2011/0112669 A1* | 5/2011 | Scharrer et al. | 700/94 |
| 2011/0125300 A1 | 5/2011 | Jaiswal et al. | |
| 2012/0209612 A1* | 8/2012 | Bilobrov | 704/270 |
| 2013/0345840 A1* | 12/2013 | Lempel et al. | 700/94 |

FOREIGN PATENT DOCUMENTS

| | | |
|---|---|---|
| WO | 2006049990 | 5/2006 |
| WO | 2007021984 | 2/2007 |

OTHER PUBLICATIONS

Wang, Avery Li-Chun, "An Industrial-Strength Audio Search Algorithm," Shazam Entertainment, Ltd., pp. 1-7 (No Date).

* cited by examiner

VIBRATION CONDITION MONITORING SYSTEM AND METHODS

BACKGROUND

The subject matter disclosed herein relates to machine maintenance techniques for industrial systems. More specifically, the subject matter disclosed herein relates to monitoring and diagnosing the mechanical condition of industrial systems based at least partially upon acoustic analyses.

Certain equipment and facilities, such as power generation equipment and facilities, oil and gas equipment and facilities, manufacturing equipment and facilities, and the like, include a plurality of interrelated systems and processes. For example, power generation plants may include turbine systems and processes for operating and maintaining the turbine systems. Likewise, oil and gas operations may include carbonaceous fuel retrieval systems and processing equipment interconnected via pipelines. During normal operations, the equipment may encounter undesired conditions (e.g., misalignment, looseness, imbalance, etc.) that may potentially affect the overall equipment performance and effectiveness. As such, it may be desirable to use condition monitoring techniques to monitor and diagnose the mechanical condition of the industrial systems.

Oftentimes, monitoring and diagnosing the mechanical condition of machine components may be complicated due to the complex nature of the machine components within the system. For example, power generation plants and oil and gas operations each involve a plurality of interrelated systems, with each system including complex and extensive machinery. Monitoring the condition of each machine component within the extensive system may involve a large amount of man power and/or time. Further, diagnosing a specific machine component failure from within a system of interrelated machine components may involve extensive knowledge, skill, or resources not readily available. Accordingly, various condition monitoring techniques may be used to monitor and diagnose machine components of industrial systems. For example, machine component failures may be monitored with a plurality of sensors disposed on the equipment, such that each sensor is configured to measure a machine condition parameter. However, it may be unwieldy and time consuming to analyze each parameter from the plurality of sensors in order to diagnose a machine component failure. Further, it may be cost-prohibitive to perform such monitoring. In certain situations, machine component failures may be monitored through vibration signal analysis, where vibration signals are indicative of a machine's mechanical condition. However, determining a machine component failure diagnosis from vibration signals often involves vibration specialists and/or specialized procedures and/or tasks. A vibration specialist visually and subjectively analyzes vibration signals, and an inaccurate and/or delayed analysis could be costly and/or time consuming. In addition, a vibration specialist may not always be readily available. Accordingly, improved systems and methods for monitoring and diagnosing the mechanical condition of equipment are desirable.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a diagnostics system is provided. The diagnostics system include a detection system configured to capture acoustic information related to an event associated with a machine component, such that the detection system associates the acoustic information with contextual information related to the machine component. The diagnostics system further includes communications circuitry configured to communicatively couple the detection system with a computing system. The computing system is coupled to a processor configured to receive the acoustic information and the contextual information from the detection system, determine one or more algorithms based at least in part on the contextual information, and retrieve and execute the one or more algorithms to extract one or more characteristic features of the acoustic information. The processor is further configured to generate an acoustic fingerprint based at least in part on the one or more characteristic features of the acoustic information, such that the one or more characteristic features correspond to the event associated with the machine component.

In another embodiment, a method is provided. The method includes capturing, via a process-based detection system, an acoustic sample related to an event associated with a machine component and correlating contextual information related to the machine component with the acoustic information from a plurality of algorithms. The method further includes selecting one or more algorithms from the plurality of algorithms that correspond at least in part to the contextual information and executing the one or more algorithms via a processor, wherein the one or more algorithms are configured to extract characteristic features of the acoustic sample. In addition, the method further provides generating an acoustic fingerprint of the acoustic sample based at least in part on the extracted characteristic features of the acoustic sample.

In yet another embodiment, another method is provided. The method includes extracting a first set of characteristic features of a first acoustic sample via one or more algorithms executed by one or more processors, and generating a first acoustic fingerprint of the first acoustic sample based at least in part on the first set of extracted characteristic features of the first acoustic sample. Further, the method includes determining an event associated with a machine component based at least in part on the first set of extracted characteristic features, and tagging the first acoustic sample with the event associated with the machine component to generate a tagged first acoustic sample and storing the first acoustic fingerprint in a database. The method further includes extracting a second set of characteristic features of a second acoustic sample via the one or more algorithms executed by the one or more processors, and generating a second acoustic fingerprint of the second acoustic sample based at least in part on the second set of extracted characteristic features of the second acoustic sample. In addition, the method includes comparing the tagged first acoustic sample with the second set of extracted characteristic features of the second acoustic sample to determine whether a match exists, wherein the match is indicative of the event associated with the machine component within the second acoustic sample.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
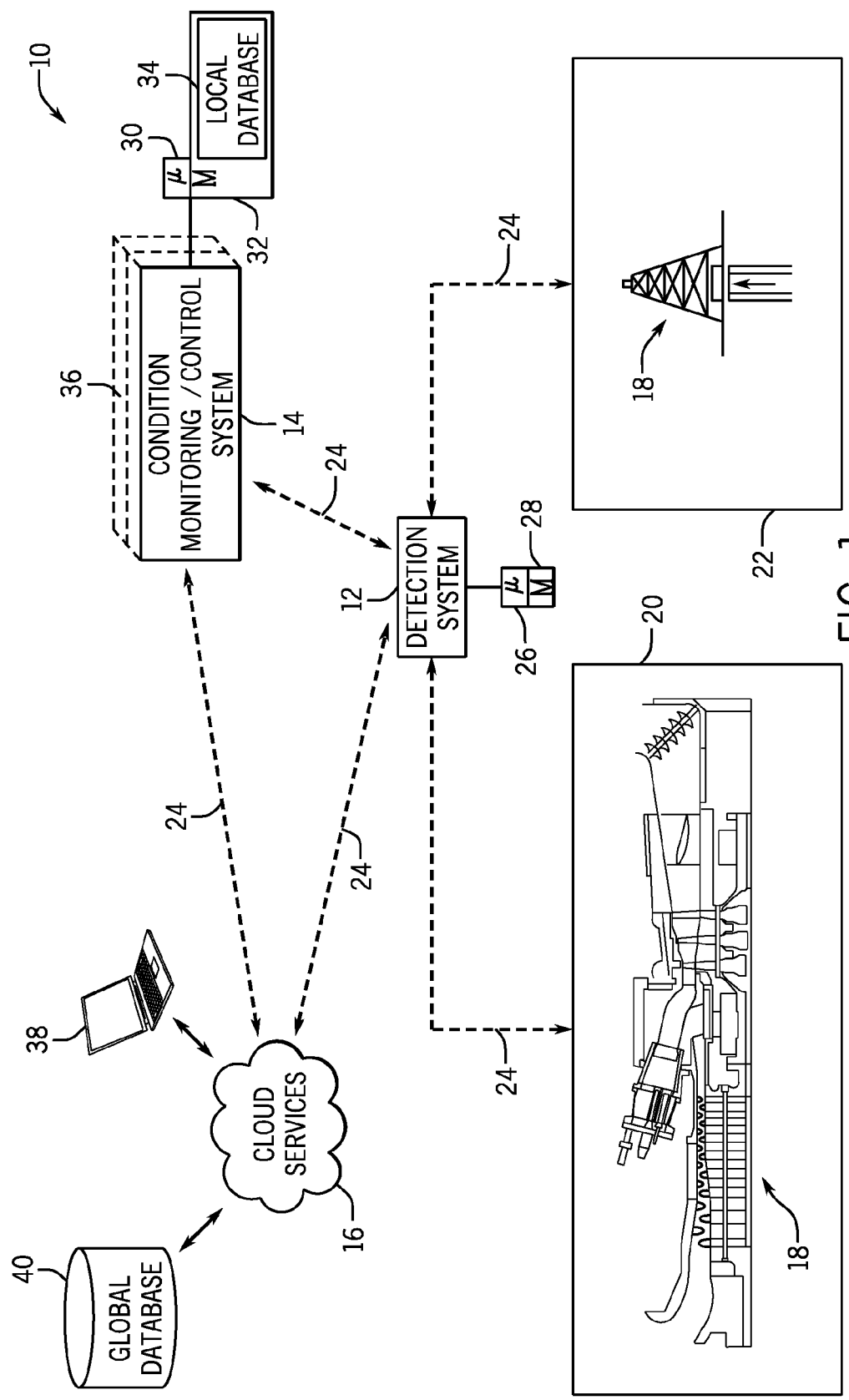
FIG. 1 is a block diagram illustrating an embodiment of a machine diagnostics system comprising a detection system, a condition monitoring/control system, and "cloud" computing services.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure generally relate to monitoring and/or diagnosing machine components of industrial systems through enhanced condition monitoring techniques. Specifically, the condition monitoring techniques described herein involve capturing audio samples (e.g., vibration data, vibration signals, etc.) of the machine components during operation, correlating contextual data (e.g., position and/or location data, time/date, machine component data, etc.) to each audio sample, analyzing the captured audio samples to extract characteristic features, and generating an acoustic fingerprint of the audio sample indicative of the extracted features. The acoustic fingerprint (e.g., acoustic signature, acoustic identifier, etc.) of the audio sample may be a content-based summary of characteristic features extracted from the audio sample. For instance, examples of characteristic features that may be algorithmically extracted from an audio sample and included in an acoustic fingerprint may include information on the frequency range, amplitude, scale factors (e.g., peak, peak-to-peak, average, displacement, etc.), spectral flatness, and so forth. In particular, the acoustic fingerprint (e.g., comprising extracted characteristic features) may be an acoustic signature configured for identification or verification functionalities.

In some embodiments, the generated acoustic fingerprint is "tagged" with the extracted features by an operator who associates the extracted features with machine component failures, and stored in one or more databases. In some embodiments, the generated acoustic fingerprint is compared with previously tagged acoustic fingerprints within the database so that a machine component and/or system failure may be detected. Indeed, the improved condition monitoring techniques described herein may provide, for example, enhanced monitoring of machine components, objective analysis of audio samples, and efficient transmission of data, thus improving the early detection of undesired conditions, minimizing machine components downtime, enhancing maintenance activities, and increasing returns on investment (ROI) of facilities and equipment.

The condition monitoring techniques involve an improved machine diagnostics system, which may include a detection system configured to capture audio samples, a condition monitoring/control system, and a data repository (e.g., "cloud" computing services or service provider communicatively coupled to a global database). In addition, the machine diagnostics system may include industrial systems (e.g., power generation plants, oil and gas operations, subsea operations, etc.) with machine components communicatively coupled to the detection system through wireless conduits. The machine components may include compressor systems and components, turbine systems and components, pumps, generators, electric motors, combustion engines, machinery such as turbomachinery, or any combination thereof. The turbine systems may include gas turbines, steam turbines, wind turbines, and hydro turbines. The detection system may be any device capable of capturing audio samples and/or vibration information from the machine components, such as mobile devices (e.g., tablets, smart phones, etc.), sensors (e.g., vibration sensors, velocity sensors, accelerometers, proximity sensors, hydrophone sensors, fiber optics sensors, etc.), cameras, microphones, USB sound capturing devices, and so forth. In particular, the detection system may be communicatively coupled through a wireless conduit to the condition monitoring/control system, other computing devices (e.g., notebooks, laptops, workstations, personal computers, etc.), or "cloud" computing services (e.g., a service provider providing cloud analytics, cloud-based collaboration and workflow systems, distributed computing systems, expert systems and/or knowledge-based systems). Furthermore, the condition/monitoring system may be communicatively coupled to a local database, while the "cloud" computing services are communicatively coupled to a global database.

With the forgoing in mind, FIG. 1 is a block diagram illustrating an embodiment of a machine diagnostics system 10, including a detection system 12, a condition monitoring/control system 14, and "cloud" computing services 16. The detection system 12 is a processor-based detection system 12 that is communicatively coupled to machine components 18 within various industrial systems. For example, the detection system 12 may be communicatively coupled through a variety of wired and/or wireless conduits 24 with machine components 18 of turbomachinery 20 (e.g. turbines, compressors, pumps, etc.) or oil and gas equipment 22. Similarly, the detection system 12 may be communicatively coupled through wired and/or wireless conduits 24 to the condition monitoring/control system 14 and/or the "cloud" computer services 16. The wireless conduits 24 may include WiFi (e.g., Institute of Electrical and Electronics Engineers [IEEE] 802.11X, cellular conduits (e.g., high speed packet access [HSPA], HSPA+, long term evolution [LTE], WiMax), near field communications (NFC), Bluetooth, personal area networks (PANs), and the like. The wireless conduits 24 may use a variety of communication protocols, such as TCP/IP, UDP, SCTP, socket layers, and so on. In certain embodiments, the wireless or wired conduits 24 may include secure layers, such as secure socket layers (SSL), virtual private network (VPN)

layers, encrypted layers, challenge key authentication layers, token authentication layers, and so on. The wired conduits 24 may include propriety cabling, RJ45 cabling, co-axial cables, fiber optic cables, and so on.

The detection system 12 may be any device capable of capturing audio samples and/or vibration data (e.g., vibration signals) from the machine components 18 of the industrial systems, and may include one or more processors 26 and a memory 28. In particular, the detection system 12 may use wireless and/or wired conduits 24 to transmit information gathered from any geographic location, including geographic locations remote from the physical location of the condition monitoring/control system 14 and/or the machine components 18. As such, the detection system 12 may be a mobile device, such as, for example, a tablet, a cell phone (e.g., smart phone), a notebook, a laptop, or any other mobile computing device with audio and/or vibration recording capabilities. In other embodiments, the detection system 12 may be any type of sensor configured to capture audio samples and/or vibration signals from the machine components 18. For example, the detection system 12 may include portable hand-held vibration meters or sensors, vibration sensors, velocity sensors, accelerometers, proximity sensors, and so forth. Additionally, the sensors may be permanently or semi-permanently (e.g., with magnetic mounts) mounted on machine components 18 to capture audio samples and/or vibration data. In such situations, the sensors may include wired or wireless capabilities, or may be functionally suitable for connecting to a device with such capabilities. The detection system 12 may also include other devices, such as, cameras, microphones, USB sound capturing devices, and so forth.

In the illustrated embodiment, machine components 18 within the turbomachinery 20 and/or the oil and gas equipment 22 (e.g., refineries, petrochemical plants, drilling sites, etc.) are generally discussed. In other embodiments, the condition monitoring techniques described herein may be used on other industrial systems, such as, for example, power plants, power and water systems (e.g., wind turbines, nuclear energy systems, etc.), aviation systems, power distribution systems, subsea operations (e.g., offshore oil and gas equipment (e.g., wellbores, drilling rigs, barges, etc.), offshore drilling, offshore mining), and so forth. Such mechanical industrial systems may experience mechanical and/or thermal stresses during operating conditions, which may require periodic machine maintenance inspections of various machine components 18. Machine components 18 within the turbomachinery 20 may include fuel nozzles, turbine nozzles, an intake, a compressor, compressor vanes, compressor blades, a turbine, turbine blades, turbine vanes, turbine or compressor wheels, a shaft, a diffuser, turbine and compressor stages, a casing, various bearings, and so forth. Likewise, machine components 18 of the oil and gas equipment 22 may include compressors, tubing, engines, pumps, rig systems, and so forth. In some situations, misalignment, mechanical looseness, structural resonance, soft foundation, shaft bow, excessive bearing wear, lost rotor, lost rotor blade, or imbalance of the machine components 18 may cause premature wear and tear. In rotary machines, such as turbomachinery, the clearance between rotary and stationary components may vary, and can potentially decrease to the point of a rub condition. For example, turbine and compressor vanes can potentially rub against a stationary shell or casing. The rub condition results in vibration. In addition, gas turbine engines may experience vibration associated with combustion dynamics in the combustors. Detecting such machine component 18 conditions and/or failures early and precisely may help to minimize machine downtime and replacement expenses. Furthermore, predicting potential machine component 18 conditions and/or failures in advance (e.g., before an actual machine component 18 failure), or predicting conditions indicative of machine component 18 failures in advance, may help minimize machine downtime and replacement expenses.

As noted above, the detection system 12 may be used to gather audio samples and/or vibration information from machine components 18 within various industrial systems. As described in detail with respect to FIGS. 3 and 4, the samples of the machine components 18 may be used to detect and repair machine component 18 failures. In particular, the audio samples and/or vibration information gathered from the machine components 18 may correspond to an event associated with the machine component 18. The event may be associated with a machine component 18 failure or defect, may be associated with conditions indicative of machine component 18 failure/defect, may be associated with conditions surrounding the machine component 18 which may be indicative of the machine component 18 defect/failure, may be associated with surrounding external environmental issues or external forces which may result in the machine component 18 defect/failure, and so forth. Indeed, the audio samples gathered by the detection system 12 may include information directly or indirectly related to the machine component 18 defect/failure.

During operation of the industrial system, the detection system 12 may be positioned on, near, or between machine components 18, and may periodically or sporadically take samples (e.g., record) from one or more machine components 18. In particular, the detection system 12 may be configured to capture samples from one or more machine components 18 in various directions (e.g., vertically, horizontally, or axially), at various angles (e.g., perpendicular to the surface), in various locations, at various times, and so forth. In addition, the detection system 12 (or another component of diagnostics system 10) may correlate contextual data to each audio sample captured, and may additionally transmit the contextual data along with the audio sample through the wired or wireless conduits 24.

The contextual data may include information relating to the position and/or location on the machine component 18 where the sample was captured (e.g., stage in the turbine or compressor, specific combustor, specific fuel nozzle, specific turbine nozzle, etc.), the time/date the sample was captured, characteristics of the machine component 18 (e.g., the machine component's running speed, a flame temperature, a load condition, a fuel type, a fuel flow rate, emission levels, exhaust temperature, ambient temperature, pressure, etc.), operating conditions of the detection system 12 (e.g., the angle or direction in which the detection system 12 is positioned during capture), and so forth. In some situations, the contextual data may also include details about the machine components 18 being sampled, such as, for example, the number of certain components within the machine, the measurements of the machine, the mounting position of the machine (e.g., vertical, horizontal, etc.), the running speed of adjacent machines, and so forth. In some situations, the contextual data may be obtained through user input into the detection system 12, such as through a keypad of a mobile device. In other situations, the contextual data may be obtained by scanning (e.g., barcode, RFID tag, etc.) a machine component 18 previously labeled and/or identified.

In certain embodiments, the detection system 12 may be communicatively coupled through wired or wireless conduits 24 to the condition monitoring/control system 14. In particular, the condition monitoring/control system 14 may be configured to receive and process the audio samples and/or vibration data from the detection system 12. The condition monitoring/control system 14 may be a computing device (e.g., laptop, personal computer, programmable logic controller (PLC), any type of controller, etc.) including and/or communicatively coupled to one or more processors 30 (e.g., processing circuitry). While the condition monitoring/control system 14 may comprise many different components, certain exemplary components are presently illustrated to demonstrate aspects in accordance with embodiments of the present techniques. Specifically, the processor 30 may be associated with a tangible, non-transitory memory 32 that allows for the storage of machine-readable instructions (e.g., control software and/or one or more algorithms used to process and analyze the captured audio samples). In certain embodiments, the control software may include condition monitoring software and/or diagnostics software platform, such as System 1® software, available from General Electric, Co., of Schenectady, N.Y. The condition monitoring/control system 14 and/or diagnostics software may be used to provide, for example, techniques for identifying, evaluating, and responding to important system events.

In particular, in certain embodiments, the memory 32 may store one or more algorithms, where each algorithm may be related, at least in part, with contextual data (e.g., position and/or location of the machine component 18 where the sample was captured, the time/date the sample was captured, characteristics of the machine component 18, operating conditions, ambient conditions, name of operator, name of facility, model number, serial number, etc.) associated with each audio or vibration sample. Upon receiving a sample, the condition monitoring/control system 14 may identify contextual information associated with the sample. In some embodiments, the system 14 may use the contextual data (e.g., date/time, location, etc.) identified to process the sample into a "trend plot" comprising current and previous data collected (e.g., historical data relating to the same machine component 18), where the previous data collected may be retrieved from the memory 32 or any other memory storage device. The processor 30 may be configured to retrieve and execute an algorithm associated with a particular type of contextual data from one or more algorithms stored in the memory 32. For example, for an audio sample taken at the rotor of a turbine, the processor 30 may retrieve and execute an algorithm associated with analyzing the samples captured from the rotor of a turbine.

One or more algorithms may be configured to extract characteristic features of the captured sample, and may be particularly configured to extract characteristic features associated with the contextual data of the sample. In certain embodiments, the features may be extracted directly from the captured sample, and in other embodiments, the features may be extracted through processing techniques, such as through time waveforms, Fast Fourier Transformation spectras, envelope detection, filtering techniques, spectral emitted energy (SEE) techniques, phase measurement techniques, high frequency detection (HFD) techniques, and other sensor resonant techniques. For example, characteristic features of the sample derived through time waveform analysis may include information on the frequency and/or frequency range, amplitude, and/or scale factors (e.g., peak, peak-to-peak, average, root mean squared (RMS) value, displacement, etc.). In other embodiments, the characteristic features of the samples derived include information on spectral flatness (e.g., an estimation of tone-like or noise-like quality within a sample), peak-based band selection (e.g., an ordered list of indexes of bands with prominent tones or peaks with significant amplitude), energy or loudness of the sample (e.g., delta and delta-delta of the energy), temporal variations within a sample (e.g., time-varying behavior of audio signals), sign of frequency and time derivatives, envelope detectors, and so forth. In certain embodiments, the executed algorithm may also include information related to the overall characteristic of the audio sample. For example, the overall vibration of a machine component may be indicative of the overall health of the machine component 18 and an abnormal overall vibration may indicate (or predict) a machine component failure. In some situations, the characteristic features of the sample may be determined by distinguishing characteristic features between current and previous data in the trend plot. Further, the executed algorithm may generate an acoustic fingerprint of the sample. The acoustic fingerprint may be indicative of the characteristic features identified, and may additionally include tags representative of the extracted characteristic features.

In some embodiments, as described in detail with respect to FIG. 3 below, the generated acoustic fingerprint may be "tagged" with the extracted features by an operator who associates the extracted features with machine component failures. For example, for the extracted features described above, such as, for example, an energy or loudness determined for the sample, an operator may associate that feature with a particular event associated with the machine component 18. As noted above, the particular event may be a machine component 18 defect/failure, conditions indicative of the machine component 18 defect/failure, surrounding conditions that are known to lead to the machine component 18 defect/failure, and so forth. The tagged acoustic fingerprint may be stored in a local database 34 within the memory 32. In other embodiments, as described in detail with respect to FIG. 4 below, the generated acoustic fingerprint is compared with previously tagged acoustic fingerprints within the local database 34, so that a machine component and/or system failure may be detected or predicted. Indeed, one or more condition monitoring/control systems 36, which implement this functionality, may be connected through network components, and may include and/or be communicatively coupled to the one or more processors 30, the memory 32 (e.g., the one or more algorithms), and the local database 34.

In some embodiments, the detection system 12 and/or the condition monitoring/control system 14 may be communicatively coupled through the wired or wireless conduits 24 to the cloud computing services 16 (e.g., cloud analytics, cloud-based collaboration and workflow systems, distributed computing systems, expert systems and/or knowledge-based systems). Further, in one embodiment, the detection system 12 may provide "hot spot" functionality in which the detection system 12 may provide wireless access point (WAP) functionality suitable for connecting the turbomachinery 20 and/or the oil and gas equipment 22 to other systems in the cloud 16, such as a computing system 38. Indeed, in some embodiments, the computing system 38 may receive and process the audio samples and/or vibration data from the detection system 12, as described with respect to the condition monitoring/control system 14. In certain embodiments, the computing system 38 may include the one or more processors 30 configured to retrieve and execute one or more algorithms based, at least in part, on the contextual data associated with an audio/vibration sample. Further, in such embodiments, the computing system 38 may include the memory 32 and the local database 34 configured to store generated tagged acoustic fingerprints.

Furthermore, the cloud computing services 16 may be coupled to a global database 40 which is also configured to store generated tagged acoustic fingerprints. In addition, the global database 40 may allow computing devices (e.g., 12, 14, 36 or 38) to retrieve previously tagged acoustic fingerprints stored in the global database 40 for additional processing and/or comparison. Indeed, the global database 40 may be accessed by a plurality of systems (e.g., detection systems 12 and/or condition monitoring/control systems 14 or 36) from any geographic location, including geographic locations remote from the physical locations of the systems. Accordingly, the cloud 16 may enable advanced collaboration methods between parties in multiple geographic areas, provide multi-party workflows, data gathering, and data analysis, which may increase the accuracy of diagnosing problems detectable by an audio sampled fingerprint.

Figure 2:
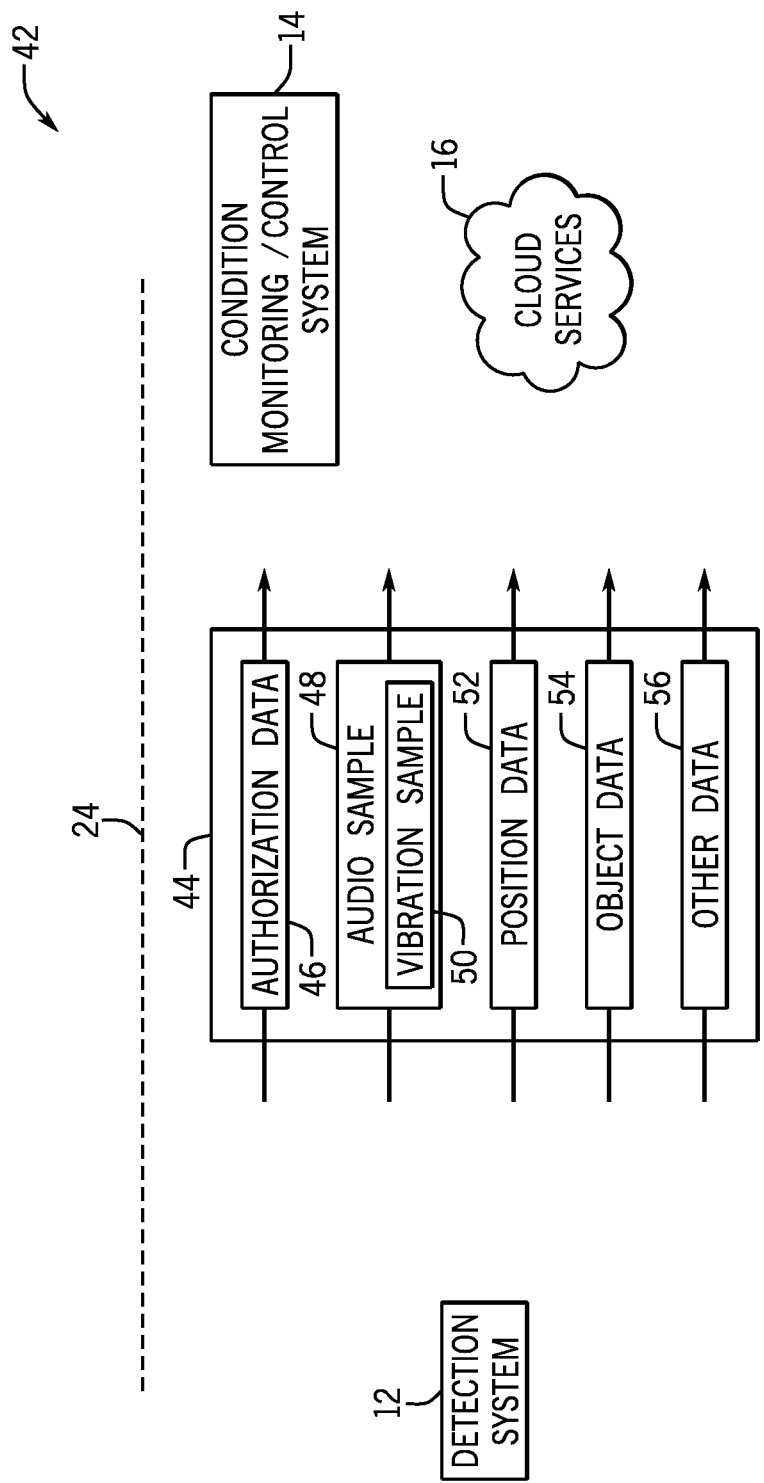
FIG. 2 is a block diagram illustrating an embodiment of information flow between the detection system and the condition monitoring/control system or a global database.

FIG. 2 is a block diagram illustrating an embodiment of information flow 42 between the detection system 12 and the condition monitoring/control system 14 and/or the cloud 16. Specifically, the illustrated embodiment depicts information that may be included in a sample 44 (e.g., audio sample, vibration signal, vibration sample, etc.) measured by the detection system 12. As mentioned above, the detection system 12 may use a wired or wireless conduit 24 to transmit data. In certain embodiments, the wireless conduit may include WiFi (e.g., 802.11X), cellular conduits (e.g., HSPA, HSPA+, LTE, WiMax), NFC, Bluetooth, PANs, and the like. The wireless conduit may use a variety of communication protocols, such as TCP/IP, UDP, SCTP, socket layers, and so on. In certain embodiments, the wireless conduit may include secure layers, such as SSL, VPN layers, encrypted layers, challenge key authentication layers, token authentication layers, and so on. Additionally, the protocols of the wired or wireless conduit 24 and/or the detection system 12 may dynamically compress data, depending on, for example, currently available bandwidth and latency. The receiving system component (e.g., condition monitoring/control system 14, cloud services 16, computing system 38, etc.) may then uncompress and display the data. Compression/decompression techniques may include H.261, H.263, H.264, moving picture experts group (MPEG), MPEG-1, MPEG-2, MPEG-3, MPEG-4, DivX, and so on.

The sample 44 may include authorization data 46 that may be used to provide authorization or login information suitable to pair or otherwise authenticate the detection system 12 to the condition monitoring/control system 14 and/or the cloud 16 or vise versa. In particular, the authorization data 46 may include identification information related to the operator, client, user, and so forth such that the sample 44 is only stored if the operator, client, or user is authorized to send samples. In certain embodiments, the authorization data 46 may be stripped from the sample 44 as the sample 44 is being processed and analyzed, and before the processed sample 44 (e.g., generated and tagged acoustic fingerprint) is stored within the local database 34 and/or the global database 40. In this manner, the origin of the sample 44 may be kept anonymous and confidential from downstream users.

In particular, the sample 44 includes an audio sample 48 that is collected from the detection system 12. As noted above, the detection system 12 may be any device capable of capturing audio samples and/or vibration data (e.g., vibration signals) from the machine components 18 of the industrial systems. Accordingly, the audio sample 48 may include sounds of the machine components 18 during operation, such as sounds of machine components 18 abutting or contacting other structures, the sounds related to flows, pressures, or temperatures of machine components, vibrations felt through the machine component 18 or through an adjacent machine component 18, combustion dynamics, and so forth. In particular, the audio sample 48 may include a vibration sample 50 that includes information on the vibrations (e.g., vibration signals) observed by the detection system 12 when measurements are captured at the machine component 18. The vibration sample 50 may be indicative of the machine component's mechanical condition (e.g., including failures or defects of the machine components 18), conditions indicative of a future machine component 18 mechanical condition, and so forth. As such, analyzing the vibration sample 50, processing the vibration sample 50 to extract characteristic features of the vibration sample 50, generating an acoustic fingerprint of the vibration sample 50 including the characteristic features, and then comparing the generated acoustic fingerprint with acoustic fingerprints of known machine component 18 defects/failures allows a system to determine a machine component 18 failure. Further, such analyzing, generating, and comparing of acoustic fingerprints may additionally allow the system to predict a future machine component 18 failure or defect. Indeed, prediction of future machine component 18 failures/defects may allow for the early detection and handling of machine component 18 defects/failures.

As noted above, in certain embodiments, the measured sample 44 may include contextual data that is associated with each sample 44 captured by the detection system. The contextual data may include information such as position data 52, object data 54, or other data 56. For example, the position data 52 may include locations of the detection system 12 in relation to the machine components 18 within the industrial systems 20/22. In addition, the position data 52 may include information relating to the location of the measurement in relation to the machine component 18, such as where the measurement was taken on the machine component 18 (e.g., stage of a turbine or compressor, a specific fuel nozzle, a specific combustor, a specific turbine nozzle, a specific bearing, etc). Techniques such as global positioning system (GPS), radio frequency identification (RFID), triangulation (e.g., WiFi triangulation, radio triangulation) may be used to determine the position data 52 of the detection system 12. Further, the measured sample 44 may include object data 54 related to the machine components 18 being measured. For example, the object data 54 may include identifying information (e.g., manufacturing data, serial numbers, barcodes, RFID tags, servicing data, facility location data, etc.) on the machine component 18, observations on equipment condition, and so forth. Further still, the measured sample 44 may include other data 56, such as data relating to the type of measurements taken (e.g., length of time of measurement, pressure applied to measurement surface, angle or skew of measurement, etc.). Further, in some embodiments, the detection system 12 may be configured to determine and extract certain characteristic features of the sample 44 before transmission, and may include the extracted features as tags associated with the sample 44 within the other data 56. In other embodiments, the position data 52, the object data 54, and other data 56 may be obtained through user input from the operator operating the detection system 12.

Figure 3:
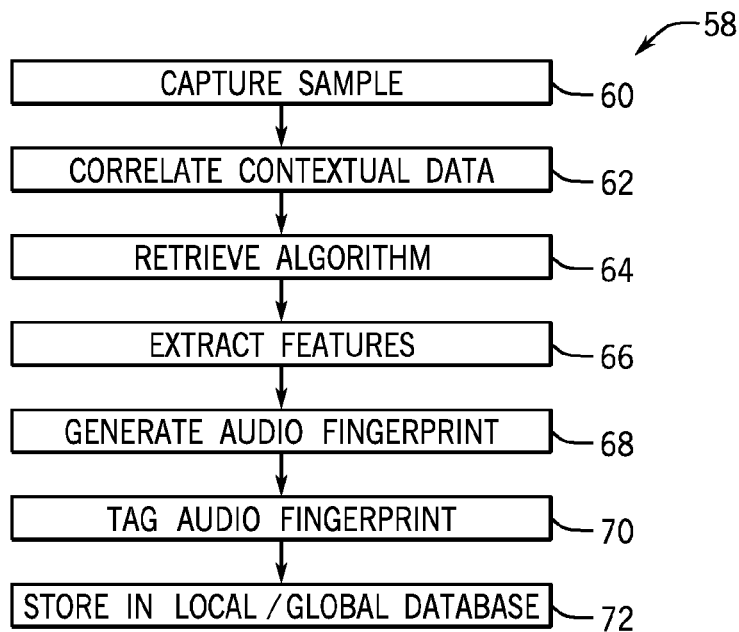
FIG. 3 is a flow chart depicting a detailed process for tagging and storing a generated acoustic fingerprint with extracted features.

FIG. 3 is a flow chart depicting a detailed process 58 for tagging the generated acoustic fingerprint with the extracted features by an operator who associates the extracted features with machine component failures. By tagging the acoustic fingerprints with known machine component failures or known conditions that likely lead to a particular machine component failure, acoustic fingerprints indicative of unknown machine component failures may be determined. In particular, the acoustic fingerprints with known machine component failures are compared with the acoustic fingerprints of unknown machine component failures, such that a match between the two is indicative of the same machine component failure.

First, the detection system 12 captures the sample 44 (e.g., the audio sample 48 including the vibration sample 50) from one or more machine components 18 (block 60). As described above, the sample 44 may be measured from machine components 18 during operation, and the sample 44 may be taken by positioning the detection system 12 on, near, or between the machine components 18 in various directions, angles, locations, times, and so forth. Upon capturing the sample 44, the detection system 12 may correlate contextual data (e.g., position data 52, object data 54, other data 56, etc.) with the sample 44 in the manner described above (block 62). For example, the contextual data may include information relating to the position and/or location on the machine component 18 where the sample 44 was captured, the time/date the sample 44 was captured, the running speed of the machine component, operating conditions of the machine component (e.g., flame temperature, fuel flow rate, emissions levels and composition, exhaust temperature, ambient temperature, load, etc.), the angle or direction in which the detection system 12 was positioned, and so forth. The contextual data may be linked with the sample 44, such that the contextual data is also transferred with the sample 44 through the wired or wireless conduits 24. In certain embodiments, the information is transmitted to the condition monitoring/control system 14 coupled to the local database, while in other embodiments, the information is transmitted to the cloud 16 coupled to the computing system 38 and the global database 40.

Upon receiving the sample 44 and the contextual data, the condition monitoring/control system 14 or the cloud 16 may identify and associate the contextual data with one or more corresponding algorithms within the memory 32. The processor 30 may be used to retrieve and execute the identified algorithm (block 64) to process and analyze the sample 44 (e.g., wherein the identified algorithm is based in part on the contextual data). The executed algorithm may be configured to extract characteristic features of the captured sample 44 (block 66). As mentioned above, in some embodiments, the executed algorithm may be particularly configured to extract features based upon the contextual data of the sample 44. In other embodiments, the executed algorithm may additionally include techniques for processing audio and/or vibration samples, such as, for example, Fast Fourier Transformation spectras, envelope detection, filtering techniques, spectral emitted energy (SEE) techniques, phase measurement techniques, high frequency detection (HFD) techniques, and other sensor resonant techniques.

Using these techniques and/or characteristic features of a sample 44 associated with contextual data, the processor 30 may be used to generate an acoustic fingerprint of the sample 44 (block 68). The acoustic fingerprint may be a condensed digital summary of the sample 44 indicative of the extracted characteristic features. In certain embodiments, the processor 30 may additionally "tag" the acoustic fingerprint with the extracted characteristics (block 70). For example, if the executed algorithm determines the frequency or amplitude of a portion of the sample 44 (e.g., a portion of the sample 44 indicative of a machine component 18 failure) as characteristic features, the acoustic fingerprint may be tagged with such information. In certain embodiments, the "tag" associated with the acoustic fingerprint may include keywords describing the features textually. In other embodiments, the "tags" may additionally include graphics (e.g., arrow pointers, crosses, highlighted regions, geometric shapes, etc.) associated with a trend plot or time waveforms. In particular, multiple algorithms may be used to process and analyze the same sample 44. In such situations, each algorithm may determine the same or different characteristics features of the sample 44, which may be tagged with the acoustic fingerprint without repetition. Processing the sample 44 with multiple algorithms (e.g., multiple processing methods) provides a comprehensive analysis of the sample 44 and multiple methods to recognize and identify system failures. Further, when comparing samples 44 processed with multiple algorithms, a greater confidence interval can be established.

In certain embodiments, in addition to a processor 30 tagging the generated acoustic fingerprint, an operator (e.g., a computer operator) may "tag" the generated acoustic fingerprint with a particular diagnosis to generate a reference acoustic fingerprint. For example, in such embodiments, the operator may analyze the features extracted from the sample 44, and may associate the extracted characteristic features with known machine component 18 failures (e.g., failures observed by the operator). For example, an operator may know of a particular error condition of a device. The operator may associate an abnormal amplitude of the acoustic fingerprint with a particular error condition, and may tag the acoustic fingerprint to indicate the same. The tagged acoustic fingerprint may be stored in the local database 34 and/or the global database 40 (block 72), thus creating an acoustic fingerprint reference for the particular error condition. In particular, the reference acoustic fingerprints stored in the local database 34 and/or the global database 40 may be a reference bank of acoustic fingerprints that may be remotely accessed and/or retrieved for further use. As described with respect to FIG. 4 below, the tagged acoustic fingerprints (i.e., reference acoustic fingerprints) may be indicative of a known system failure, error condition, or defect, and may be compared with generated acoustic fingerprints that are not associated with a particular system failure or defect, for subsequent diagnosis.

Figure 4:
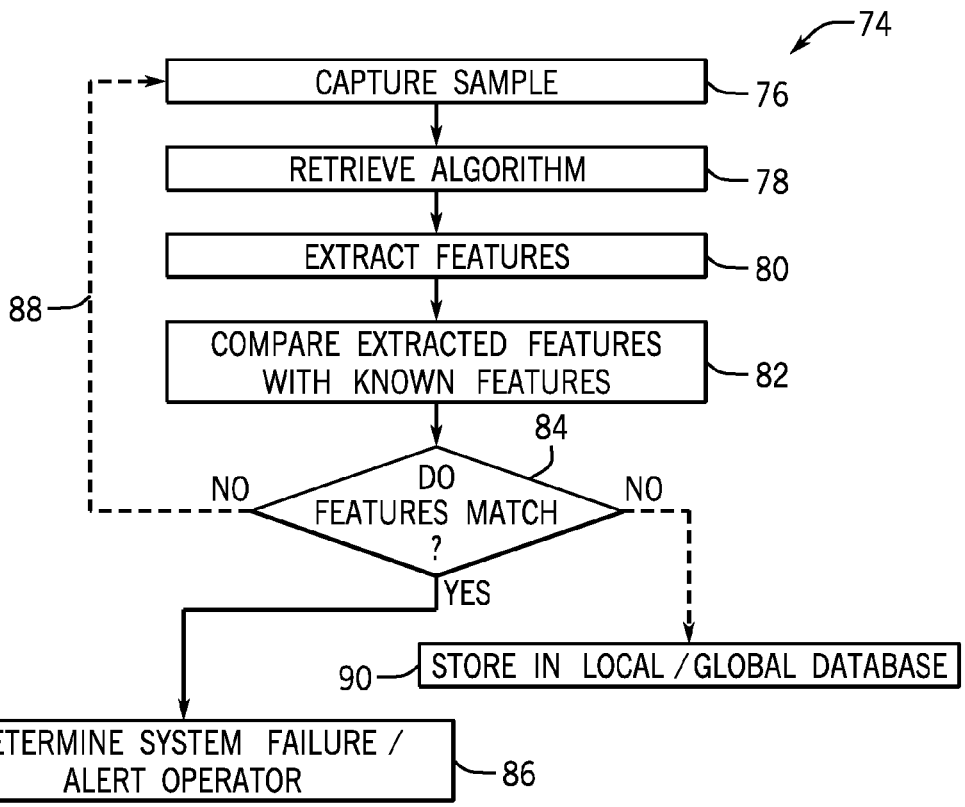
FIG. 4 is a flow chart depicting a detailed process for comparing the extracted features of the generated acoustic fingerprint to previously tagged and stored acoustic fingerprints.

FIG. 4 is a flow chart depicting a detailed process 74 for comparing the extracted features of a new acoustic fingerprint to previously tagged and stored acoustic fingerprints within the local database 34 and/or the global database 40. Specifically, machine component 18 failures or defects may be determined by comparing a fingerprint associated with a known system failure or defect with a fingerprint of unknown system failure or defect.

First, the detection system 12 captures the sample 44 (e.g., the audio sample 48 including the vibration sample 50) from one or more machine components 18 (block 76). As described above, the detection system 12 may correlate contextual data (e.g., position data 52, object data 54, other data 56, etc.) with the sample 44 before transmitting the information to the condition monitoring/control system 14 and/or the cloud 16. The system receiving the sample 44 with the contextual data may associate the contextual data with one or more algorithms and/or may use the contextual data in a selected algorithm. The processor 30 may be configured to retrieve and execute the algorithm (block 78) to extract characteristic features of the captured sample 44 (block 80).

Upon determining characteristic features of the sample 44, an acoustic fingerprint may be generated by the processor 30. In particular, the acoustic fingerprint may be a condensed digital summary of the sample 44 indicative of the extracted characteristic features, and may further be tagged with the characteristic features. In particular, the generated acoustic fingerprint with the characteristic features may be compared with previously generated and tagged acoustic fingerprints (i.e., reference acoustic fingerprints) stored within the local and/or global database (block 82) to determine a match. In particular, a match between a generated acoustic fingerprint and a reference acoustic fingerprint may correspond to a commonality of extracted characteristic features. In certain embodiments, the processor 30 may compare only the textual tags (e.g., keywords) associated with the generated fingerprint with the textual tags associate with the previously generated fingerprints. In other embodiments, the processor 30 may additionally compare other forms of tags, such as the graphical arrow pointers, geometric shapes, highlighted regions, etc.) associated with the sample 44. The processor 30 may optimally determine if the compared features match within a particular confidence interval (block 84). The confidence interval may be between approximately 95% and 99%, between approximately 80% and 94%, between approximately 60% and 79%, or may be defined through user input. With a successful match within the selected confidence interval, the condition monitoring/control system 14 and/or the computing system 38 may determine that the generated fingerprint has the same system failure or machine component 18 failure as the previously generated fingerprints. In some embodiments, upon determining one or more matches within the confidence interval, the systems may compare the results with one another for a higher confidence interval to determine a closer match between the generated acoustic fingerprint and the reference fingerprint.

Upon determining a match between the generated acoustic fingerprint and the one or more reference acoustic fingerprints, the generated fingerprint may be tagged and stored within the local database 34 and/or the global database 40. For example, the generated fingerprint may be tagged with the confidence interval determined as well as the reference acoustic fingerprints used to determine the confidence interval. In some embodiments, in the event that a processor is not able to determine a match between the characteristic features within a particular confidence interval, another sample 44 may be captured by the detection system 12 for processing and analyzing. In such situations, the sample 44 without a determined match may be stored within the local database 34 and/or the global database 40 for further investigation at a later time. For example, this sample 44 may be compared at a later time to reference acoustic fingerprints to generate a match within the desired confidence interval. In other embodiments, the generated acoustic fingerprint without a match may be determined by an operator as indicative of a previously undetermined system failure. Accordingly, the generated acoustic fingerprint is tagged and stored in a local database 34 and/or global database 40 for future use (block 90) and/or additional analysis.

The operator (e.g., computer or human operator) may be alerted by the machine diagnostics system 10 for various system functions. For example, as multiple machine components 18 failures or as predictions of future machine component 18 failures are indicated (e.g., a match within a desired confidence interval is established between the generated acoustic fingerprint and the reference acoustic fingerprint), an operator is alerted by the system 10. Further, the operator may be alerted upon a failure to match between the generated acoustic fingerprint and the reference acoustic fingerprint, upon a match within a specified confidence interval, and so forth.

Technical effects of the invention include a machine diagnostics system configured to capture acoustic information related to a machine component defect during operation of the machine components. In particular, the diagnostics system analyzes each captured acoustic sample to extract characteristic features of the acoustic sample, such that the characteristic features may be indicative of a machine component defect. In certain embodiments, the extracted characteristic features may be indicative of predictions of future machine component 18 defects). Further, the diagnostics system generates an acoustic fingerprint based on the extracted features. In some embodiments, the generated acoustic fingerprint is "tagged" by an operator who is able to associate the extracted characteristics with a particular machine error condition, thus creating an acoustic fingerprint reference for the particular machine error condition in a local database, a global database, or both. In other embodiments, the generated acoustic fingerprint is compared to previously generated and stored acoustic fingerprints tagged by an operator to determine a match. In such embodiments, a match between the generated acoustic fingerprint and the stored reference acoustic fingerprint within a particular confidence interval may be indicative of the same machine error condition.

As such, the diagnostics system described herein provides improved condition monitoring techniques that provide efficient and objective analysis of captured acoustic information. Further, the provided techniques provide for a data repository (e.g., reference bank) of acoustic fingerprints, each associated with one or more machine error conditions. Examples of acoustic fingerprints include, but are not limited to, acoustic fingerprints indicative of a rub condition (e.g., between compressor or turbine blades and a shroud), a bearing failure, a flashback condition and/or flame holding condition in a combustor, combustion dynamics, a cracked turbine or compressor blade, a damaged seal, an inlet guide vane (IGV) failure, a blockage in a fuel or air path, or another condition in a turbine, compressor, or pump. The reference bank may be remotely accessed to retrieve and compare generated acoustic fingerprints with reference acoustic fingerprints, thus improving early detection or prediction of undesired conditions within industrial systems, minimizing machine components downtime, enhancing maintenance and condition monitoring activities, and increasing returns on investment (ROI) of facilities and equipment.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A diagnostics system, comprising:
a detection system configured to capture a first set of acoustic information related to an event associated with a machine component, wherein the detection system associates the first set of acoustic information with contextual information related to the machine component;
a computing system communicatively coupled to the detection system via communications circuitry, wherein the computing system comprises a processor configured to:
receive the first set of acoustic information and the contextual information from the detection system;
select one or more algorithms based at least in part on the contextual information;
retrieve and execute the one or more algorithms to extract one or more characteristic features of the first set of acoustic information;

generate a first acoustic fingerprint based at least in part on the one or more characteristic features of the first set of acoustic information, wherein the one or more characteristic features of the first set of acoustic information corresponds to the event associated with the machine component;

receive a second set of acoustic information from the detection system and extract one or more characteristic features of the second set of acoustic information to generate a second acoustic fingerprint; and compare the first acoustic fingerprint with the second acoustic fingerprint to determine whether a match exists, wherein the match between the first and second acoustic fingerprints indicates a likelihood that the event associated with the machine component has reoccurred.

2. The system of claim 1, wherein the machine component is a component of an industrial system.

3. The system of claim 1, wherein the processor or an operator is configured to tag the first acoustic fingerprint with the one or more extracted characteristic features extracted from the first set of acoustic information to generate a tagged acoustic fingerprint.

4. The system of claim 3, wherein the tagged acoustic fingerprint is stored in a local database, a global database, or both.

5. The system of claim 1, comprising a service provider, wherein the communications circuitry is configured to communicatively couple the detection system with the service provider configured to obtain generated acoustic fingerprints from a plurality of computing systems.

6. The system of claim 5, wherein the service provider comprises a cloud-based service provider coupled to a global database, wherein the cloud-based service provider is configured to store a data repository of the generated acoustic fingerprints.

7. The system of claim 1, wherein the detection system comprises a mobile device, one or more sensors, a camera, a microphone, a hydrophone, a fiber optic sensor, a sound capturing device, or a combination thereof.

8. A method, comprising:
capturing, via a processor-based detection system, a first acoustic sample related to an event associated with a machine component;
correlating contextual information related to the machine component with the first acoustic sample;
selecting one or more algorithms from a plurality of algorithms that correspond at least in part to the contextual information;
executing the one or more algorithms via a processor, wherein the one or more algorithms are configured to extract a first set of characteristic features of the first acoustic sample;
generating a first acoustic fingerprint of the first acoustic sample based at least in part on the extracted first set of characteristic features of the first acoustic sample;
capturing, via the processor-based detection system, a second acoustic sample and extracting a second set of characteristic features of the second acoustic sample via the one or more algorithms to generate a second acoustic fingerprint; and
comparing the first acoustic fingerprint with the second acoustic fingerprint to determine whether a match exists, wherein the match between the first and second acoustic fingerprints indicates a likelihood that the event associated with the machine component has reoccurred.

9. The method of claim 8, comprising tagging the first acoustic fingerprint with the extracted first set of characteristic features, wherein the first set of extracted characteristic features are representative of the event associated with the machine component.

10. The method of claim 8, comprising determining the event associated with the machine component, and tagging the first acoustic fingerprint with the event associated with the machine component.

11. The method of claim 10, comprising tagging a rub condition, a misalignment, a mechanical looseness, a structural resonance, a soft foundation, a shaft bow, a bearing wear, a lost rotor blade, an imbalance, a flashback event, a flame holding event, a combustion dynamics event, a crack event, or a combination thereof, as the event associated with the machine component.

12. The method of claim 10, comprising storing the first acoustic fingerprint tagged with the event associated with the machine component in a local database, a global database, or both.

13. The method of claim 8, wherein the contextual information comprises information relating to a position of the detection system, a date, a time, a location, a running speed, an angle, or a combination thereof, with the first acoustic sample.

14. The method of claim 8, comprising defining the contextual information to the detection system through user input.

15. The method of claim 8, wherein the first set of characteristic features of the first acoustic sample comprises a frequency, a frequency range, an amplitude, one or more scale factors, or a combination thereof.

16. The method of claim 8, comprising generating a historical trend based at least in part on the first acoustic sample and the contextual data.

17. A method, comprising:
extracting a first set of characteristic features of a first acoustic sample via one or more algorithms executed by one or more processors;
generating a first acoustic fingerprint of the first acoustic sample based at least in part on the first set of extracted characteristic features of the first acoustic sample;
determining an event associated with a machine component based at least in part on the first set of extracted characteristic features;
tagging the first acoustic sample with the event associated with the machine component to generate a tagged first acoustic sample;
storing the first acoustic fingerprint in a database;
extracting a second set of characteristic features of a second acoustic sample via the one or more algorithms executed by the one or more processors;
generating a second acoustic fingerprint of the second acoustic sample based at least in part on the second set of extracted characteristic features of the second acoustic sample; and
comparing the tagged first acoustic sample with the second set of extracted characteristic features of the second acoustic sample to determine whether a match exists, wherein the match is indicative of the event associated with the machine component within the second acoustic sample.

18. The method of claim 17, comprising retrieving the first acoustic fingerprint from the database; and comparing the first acoustic fingerprint with the second acoustic fingerprint to determine whether the match exists.

19. The method of claim 17, comprising alerting an operator if the first acoustic sample matches the second acoustic sample within a confidence interval.

20. The method of claim 19, comprising storing the second acoustic sample within the database if the first acoustic sample does not match the second acoustic sample within the confidence interval.

* * * * *